(12) United States Patent
Manotas, Jr.

(10) Patent No.: US 8,063,786 B2
(45) Date of Patent: Nov. 22, 2011

(54) METHOD OF DETECTING DROWSINESS OF A VEHICLE OPERATOR

(75) Inventor: Jesus Manotas, Jr., Peachtree City, GA (US)

(73) Assignee: Panasonic Automotive Systems Company of America division of Panasonic Corporation of North America, Peachtree City, GA (US)

( * ) Notice: Subject to any disclaimer, the term of this patent is extended or adjusted under 35 U.S.C. 154(b) by 339 days.

(21) Appl. No.: 12/380,096

(22) Filed: Feb. 24, 2009

(65) Prior Publication Data

US 2010/0214105 A1 Aug. 26, 2010

(51) Int. Cl.
*G08B 23/00* (2006.01)

(52) U.S. Cl. ......... 340/576; 340/575; 340/439; 382/118

(58) Field of Classification Search .................. 340/575, 340/576, 439, 937, 573.1, 5.83, 539.12; 180/272; 382/118, 104; 701/1, 41, 45; 348/148, E7.085
See application file for complete search history.

(56) References Cited

U.S. PATENT DOCUMENTS

| | | | |
|---|---|---|---|
| 7,027,621 B1 * | 4/2006 | Prokoski ....................... 382/118 |
| 7,423,540 B2 * | 9/2008 | Kisacanin ..................... 340/576 |
| 7,821,409 B2 * | 10/2010 | Ishida ........................... 340/576 |

* cited by examiner

*Primary Examiner* — Anh V La
(74) *Attorney, Agent, or Firm* — Laurence S. Roach (57) ABSTRACT

A method of rectifying drowsiness of a vehicle driver includes capturing a sequence of images of the driver. It is determined, based in the images, whether a head of the driver is tilting away from a vertical orientation in a substantially lateral direction toward a shoulder of the driver. The driver is awakened with sensory stimuli only if it is determined that the head of the driver is tilting away from a vertical orientation in a substantially lateral direction toward a shoulder of the driver.

20 Claims, 7 Drawing Sheets

METHOD OF DETECTING DROWSINESS OF A VEHICLE OPERATOR

BACKGROUND OF THE INVENTION

1. Field of the Invention

The present invention relates to methods for sensing when a person is about to fall asleep, and, more particularly, to methods for sensing when a vehicle operator is about to fall asleep.

2. Description of the Related Art

The U.S. National Highway Traffic Safety Administration estimates that approximately 100,000 police-reported crashes annually, about 1.5% of all crashes, involve drowsiness or fatigue as a principal factor. Drowsiness/fatigue may play a role in crashes attributed to other causes. About one million crashes annually (one-sixth of all crashes) are thought to be produced by driver inattention or lapses.

Systems for detecting driver sleepiness and alerting the drowsy driver have been developed. One such system works only if the driver's head falls forward and requires wearing a device on the driver's ear. In the case of the head falling sideways, the fluid-based mercury switch sensors of these known systems fail to trigger an alarm.

Another problem with these known driver sleepiness detection systems is that they trigger false alarms in the event that the driver intentionally tilts his head forward, such as if the driver looks at the floor in front of the driver's seat. That is, there is no second criterion used to verify the drowsiness of the driver.

Other known driver sleepiness detection systems determine a degree of driver drowsiness based upon a frequency and/or duration of the closure of the driver's eyelids. These systems sense eyelid closure based on a change in pixel color of given areas within a camera's field of view. A problem with such systems is that they may often erroneously decide that they have detected eye closure in response to changing lighting conditions within the passenger compartment of the vehicle or in response to the driver moving his head.

Accordingly, what is neither anticipated nor obvious in view of the prior art is a method of detecting driver drowsiness in response to the driver's head falling sideways. What is also neither anticipated nor obvious in view of the prior art is a method of detecting driver drowsiness based on both head movement and a second criterion that confirms the driver's drowsiness. What is further neither anticipated nor obvious in view of the prior art is a method of detecting driver drowsiness based on detected eye closure that is less likely to trigger false alarms in response to a change in passenger compartment lighting or to movement of the driver's head.

SUMMARY OF THE INVENTION

The present invention provides methods for determining levels of driver drowsiness based on analyzing changes in a sequence of captured computer vision images of the driver. If driver drowsiness is determined, a loud audible alarm may be activated in order to fully awaken the driver.

In one embodiment, the inventive system alerts the user when the driver's head falls in any direction for a period of about two to three seconds, indicating driver drowsiness. In another embodiment, the inventive system uses edge detection to determine driver drowsiness based on an increased frequency and/or duration (e.g., two to three seconds) of eyelid closures. In yet another embodiment, the inventive system determines driver drowsiness based on a combination of the driver's head falling in any direction and an increased frequency and/or duration of driver eyelid closure.

The invention comprises, in one form thereof, a method of rectifying drowsiness of a vehicle driver, including capturing a sequence of images of the driver. It is determined, based in the images, whether a head of the driver is tilting away from a vertical orientation in a substantially lateral direction toward a shoulder of the driver. The driver is awakened with sensory stimuli only if it is determined that the head of the driver is tilting away from a vertical orientation in a substantially lateral direction toward a shoulder of the driver.

The invention comprises, in another form thereof, a method of rectifying drowsiness of a vehicle driver, including capturing a sequence of images of the driver. Edge detection is used on the images to determine whether a head of the driver is tilting away from a vertical orientation, and/or whether a frequency or a duration of eyelid closure of the driver is indicative of drowsiness of the driver. The driver is awakened with sensory stimuli if either it is determined that the head of the driver is tilting away from a vertical orientation, or it is determined that the frequency or duration of eyelid closure of the driver is indicative of drowsiness of the driver.

The invention comprises, in yet another form thereof, a method of rectifying drowsiness of a vehicle driver, including capturing a sequence of images of the driver. It is determined, based in the images, whether a head of the driver is tilting away from a vertical orientation. It is ascertained, based in the images, whether a frequency or a duration of eyelid closure of the driver is consistent with drowsiness of the driver. The driver is awakened with sensory stimuli only if it is determined that the head of the driver is tilting away from a vertical orientation, and it is ascertained that the frequency or duration of eyelid closure of the driver is consistent with drowsiness of the driver.

An advantage of the present invention is that the driver does not have to wear any device on his body in order for his level of drowsiness to be accurately determined.

Another advantage of the present invention is that driver drowsiness can be detected in response to the head falling in any direction.

Yet another advantage is that driver drowsiness can be more accurately detected based upon frequency and/or duration of eye closures.

A further advantage is that detection of driver drowsiness can be based on both sensing that the driver's head has fallen and that his eyelid closures have increased in duration and/or frequency. Thus, driver drowsiness may be sensed with greater sensitivity and with few false alarms.

BRIEF DESCRIPTION OF THE DRAWINGS

The above-mentioned and other features and objects of this invention, and the manner of attaining them, will become more apparent and the invention itself will be better understood by reference to the following description of embodiments of the invention taken in conjunction with the accompanying drawings, wherein.

DETAILED DESCRIPTION

The embodiments hereinafter disclosed are not intended to be exhaustive or limit the invention to the precise forms disclosed in the following description. Rather the embodiments are chosen and described so that others skilled in the art may utilize its teachings.

Figure 1:
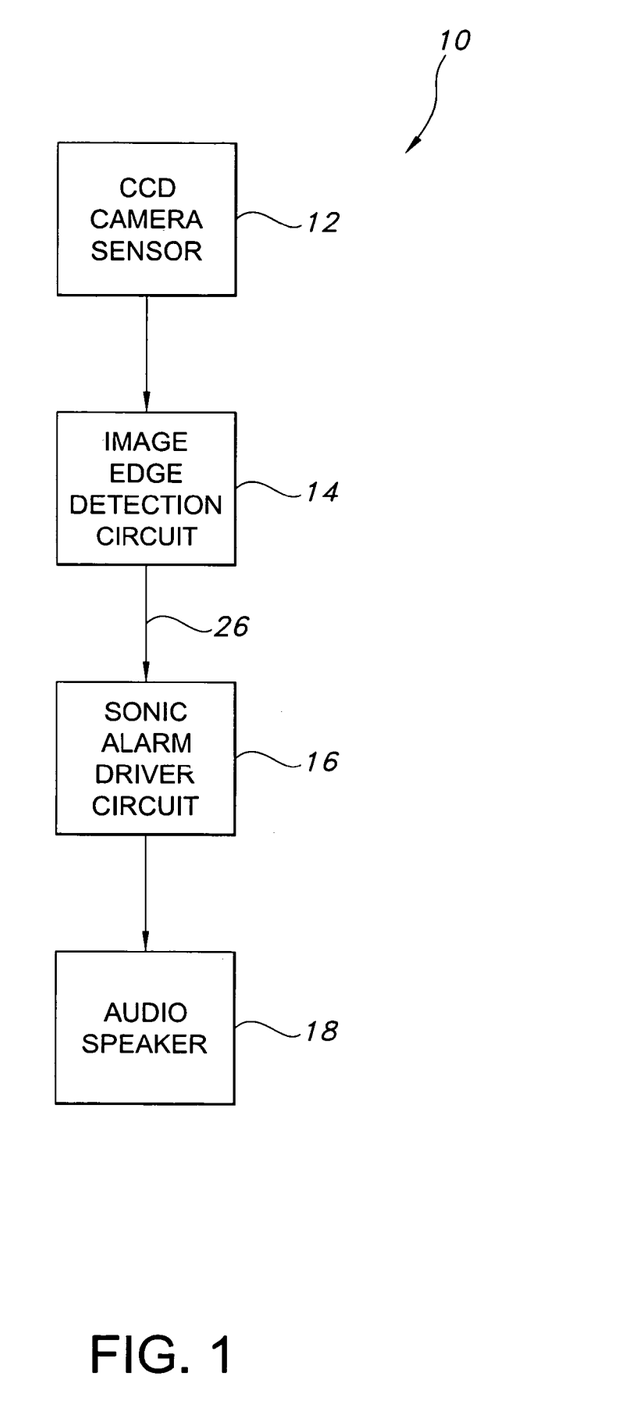
FIG. 1 is a block diagram of one embodiment of a vehicle driver drowsiness rectification system of the present invention.

Referring now to the drawings, and particularly to FIG. 1, there is shown one embodiment of a vehicle driver drowsiness rectification system 10 of the present invention including a charge-coupled device (CCD) camera sensor 12, an image edge detection circuit 14, a sonic alarm driver circuit 16, and an audio speaker 18. System 10 may be a stand alone, discrete unit that is placed on a vehicle dashboard, or system 10 may be integrated into the dashboard. The vehicle in which system 10 operates may be an automobile, airplane, boat, or any other type of vehicle.

Camera sensor 12 may be oriented such that camera sensor 12 captures images of the head of the driver, and, in some embodiments, particularly one or both of the driver's eyes. Thus, camera sensor 12 may have a lens whose focal point coincides with, or may be focused to coincide with, the head of the driver. In some embodiments, camera sensor 12 is focused on one or both of the driver's eyes.

Image edge detection circuit 14 may be in the form of a Nvidia AXP 2500 system-on-chip (SOC) mobile applications processor. That is, circuit 14 may include a camera interface and image processing software running on a computer processing unit (CPU) or graphics processing unit (GPU) such as the APX 2500 applications processor marketed by NVIDIA Corporation. However, the system of the invention can be used along with any choice of graphics processor. Detection of motion of the driver's head and eyelids may also employ software made available by NVIDIA, such as NVIDIA's GpuCV software.

Circuit 14 may use an edge detection algorithm, such as a Laplacian algorithm or other proprietary algorithm, to detect the driver's eyelid closure. Alternatively, or in addition, edge detection may be used to determine the positions and movements of the driver's open eyes as he moves his head. It is also possible for edge detection to be used to sense tilting of the driver's head, such as by detecting movements of the edge of the driver's head. However, it is to be understood that some embodiments of the invention do not include edge detection, but rather employ other techniques, such as a movement detection algorithm.

In general, circuit 14, regardless of whether it employs edge detection, senses whether the driver is falling asleep. In one embodiment, tilting of the driver's head beyond a threshold amount in any direction, forward, backward, or laterally, combined with increased frequency or duration of closure of the driver's eyelid(s) results in a determination of driver drowsiness. This embodiment may advantageously have a low rate of false alarms because it relies on more than one criterion to determine driver drowsiness. That is, the frequency and/or duration of a driver's eyelid closures may increase for reasons other than sleepiness, which could result in a false alarm. For example, the driver's eye(s) being irritated by any foreign substance, such as a speck of dirt, may result in increased frequency and duration of driver eye closures. By the same token, tilting of the driver's head may occur for reasons other than sleepiness. For example, the driver may look down on the floor to search for something, may tilt his head backward in order to look at the sky, or may tilt his head laterally in order to shift his line-of-sight.

Figure 2A:
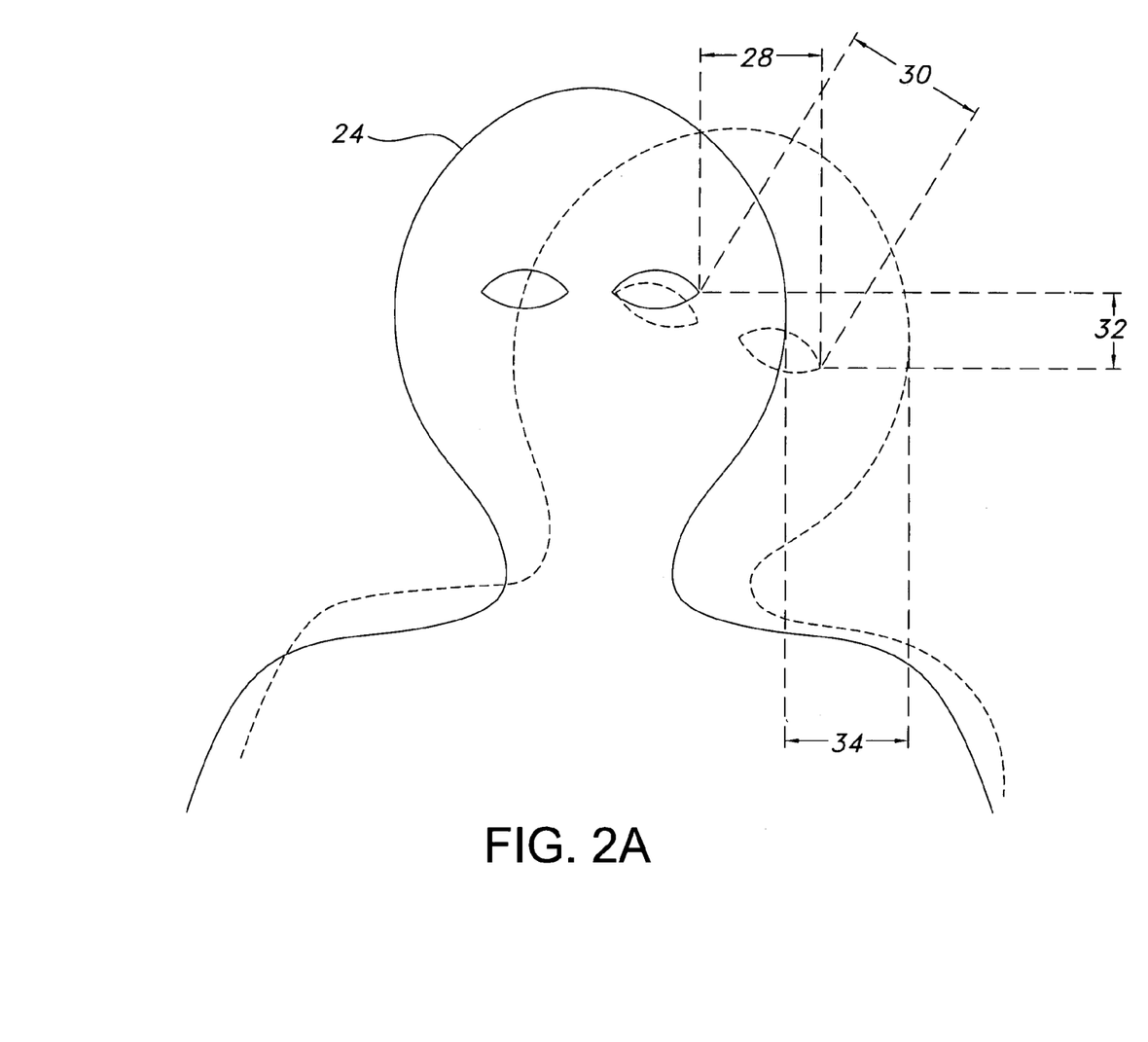
FIG. 2a is a plan view of a driver's head in an untilted position and tilted positions as sensed by the system of FIG. 1.
Figure 2B:
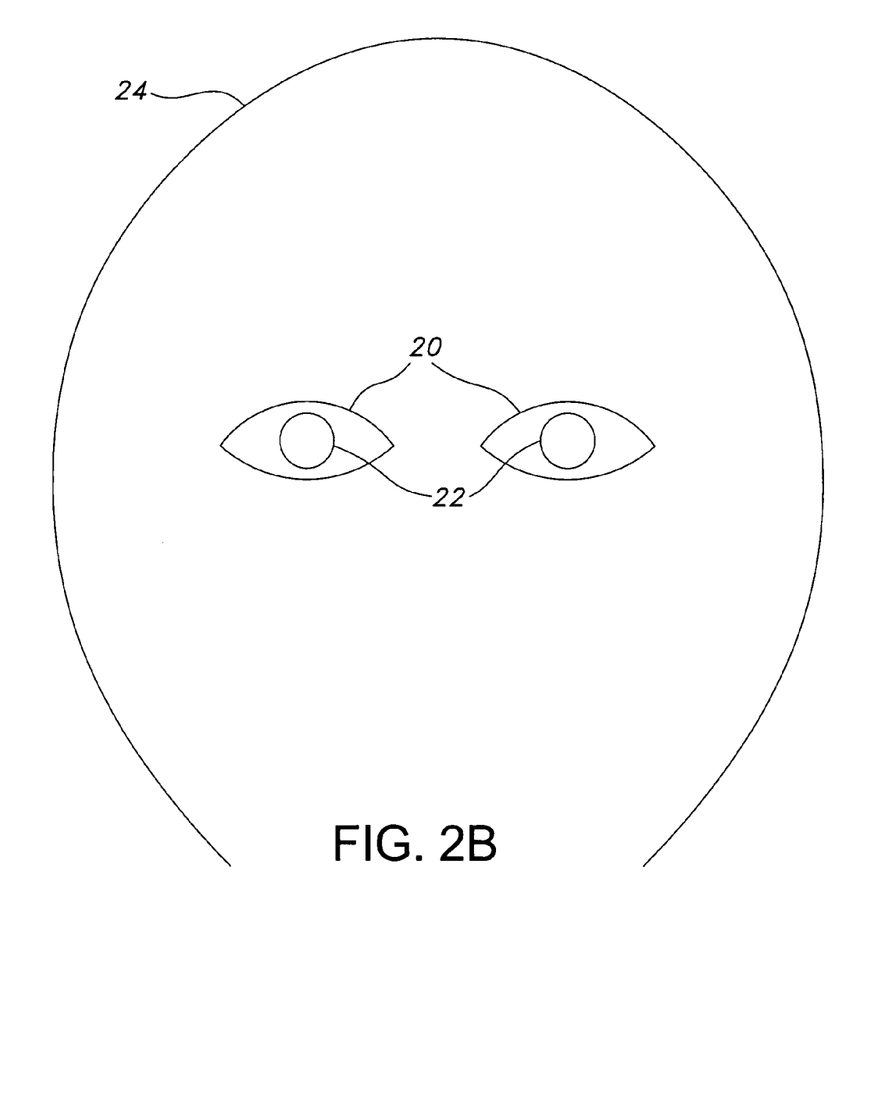
FIG. 2b is an enlarged view of the driver's head of FIG. 2a in an untilted position.

In another embodiment, the driver drowsiness determination is based exclusively upon the driver's head tilting in a lateral direction beyond a threshold amount toward a shoulder of the driver. FIGS. 2a and 2b illustrate some parameters of the driver's head and eye positions that may be sensed by camera sensor 12 and circuit 14. In particular embodiments, edge detection is used to sense edges 20 between the white portions of the driver's eyes and the driver's eyelids or skin. Alternatively, or in addition, edge detection is used to sense circular edges 22 between the white portions of the driver's eyes and the pupils of the eyes. It is also possible for edge detection to be used to detect an edge 24 between the driver's head and the background scene within the passenger compartment.

Regardless of whether the image processing includes edge detection or not, the sequence of captured images may be analyzed to determine various position parameters of the driver's eyes and head to thereby evaluate the likelihood that the driver is drowsy. If the likelihood of driver drowsiness is deemed to be above some threshold value, then the image processing circuit may transmit an alarm signal on alarm bit line 26. Sonic alarm driver circuit 16 may include a power MOSFET that is turned on by the alarm signal. In response to the MOSFET being turned on, circuit 16 may apply a signal to audio speaker 18, which may be a piezoelectric speaker, to thereby cause speaker 18 to emit sensory stimuli in the form of an audible sound suitable for awakening the driver and rectifying his drowsiness.

In general, an alarm signal may be transmitted in response to sensing that the head of the driver is tilting away from the vertical orientation (illustrated in solid lines in FIGS. 2a and 2b) in a lateral direction toward a shoulder of the driver, as illustrated in dashed lines in FIG. 2a. The sensing of the head movement may be based on ascertaining changes in a location of the driver's eye(s). In one specific embodiment, an alarm signal is transmitted in response to sensing that an outer edge of the driver's eye has moved a horizontal distance 28, or a total distance 30, that exceeds a threshold distance. In another embodiment, an alarm signal is transmitted in response to sensing that an edge of the driver's eye has dropped a vertical distance 32 that exceeds a threshold distance. In yet another embodiment, an alarm signal is transmitted in response to sensing that an outer edge of the driver's head has moved a horizontal distance 34 that exceeds a threshold distance.

In another embodiment, a novel feature of the present invention is that it may use artificial intelligence to detect both head movement and eyelid closure that indicate the driver has fallen asleep after a two to three second delay, thus reducing false alarms. Thus, not only are two different criteria used to evaluate driver drowsiness, but also one or both of the criteria must be satisfied for significant length of time before an alarm signal is transmitted.

Figure 3:
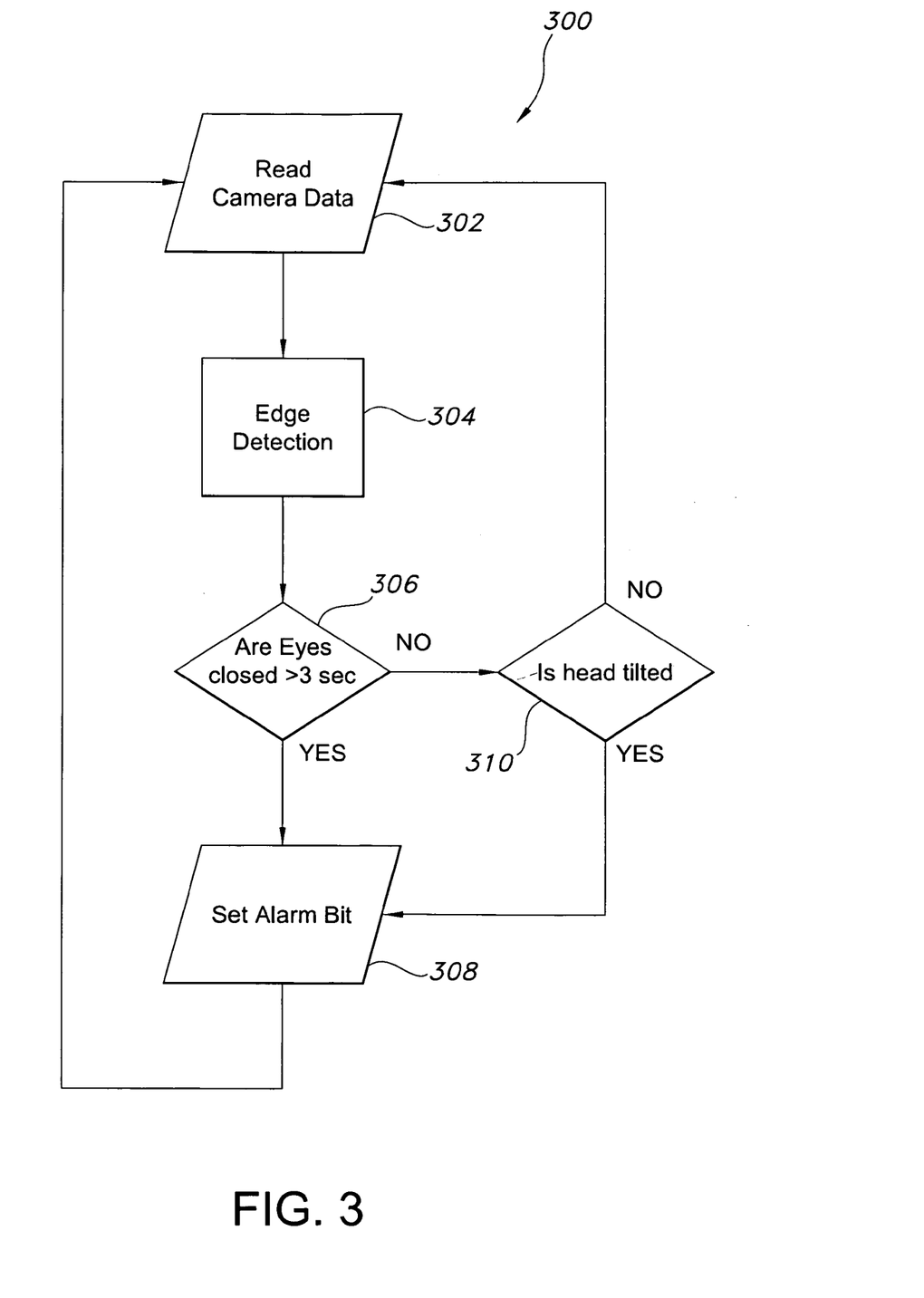
FIG. 3 is a flow chart of one embodiment of a driver drowsiness rectification method of the present invention.

One embodiment of a method 300 of the present invention for rectifying drowsiness of a vehicle operator is illustrated in FIG. 3. In a first step 302, camera data is read. For example, CCD camera sensor 12 may capture images of the head of a driver of a vehicle. In particular embodiments, the captured images may include only the eye area of the driver's head, or an edge portion of the driver's head.

In step 304, an edge detection image processing algorithm is applied to the camera data reading step 302. That is, locations of edges 20 between the whites of the eye(s) and the eyelid(s) and/or skin; edges 22 between the whites of the eye(s) and the pupil(s); and/or edge 24 between the perimeter of the driver's head and the background scene may be identified in the sequence of captured images.

In a next step 306, it is determined whether the driver's eyes have been closed for more than three seconds. In one embodiment, after the whites of the eyes have been located and the image processing algorithm has determined that the eyelids are closed, then the algorithm waits three seconds and checks the immediately preceding three seconds of images to determine whether the eyes have remained closed. If so, then driver drowsiness is confirmed and operation proceeds to step 308, where the alarm bit is set, as at 26 in FIG. 1.

In response to the alarm bit being set in step 308, audio speaker 18 may be activated in order to awaken the driver. However, it is to be understood that any type of sensory stimuli such as light, fans, etc., that awaken the driver may be employed. Operation then returns to steps 302, 304 and 306. If it is determined in steps 306 and 310 that the driver's eyes are no longer closed and his head is no longer tilted, then the sensory stimuli may be stopped.

If it is not determined in step 306 that the driver's eyes have been closed for more than three seconds, then operation proceeds to step 310, where it is determined whether the driver's head is tilted. The tilting of the driver's head may be determined in step 310 based upon the locations of the driver's eyes, the locations of the perimeter of the driver's head, or a combination of the two. It is to be understood that it is possible for operation of step 310 to proceed concurrently with and during the three second period in which the duration of eye closure is measured in step 306.

If it is determined in step 310 that the driver's head is not tilted, then operation returns to step 302 and more camera data is read. However, if it is determined in step 310 that the driver's head is tilted, then operation proceeds to step 308, where the alarm bit is set. Awakening stimuli may be provided, and the driver's state of drowsiness may be reevaluated, as described above.

Figure 4:
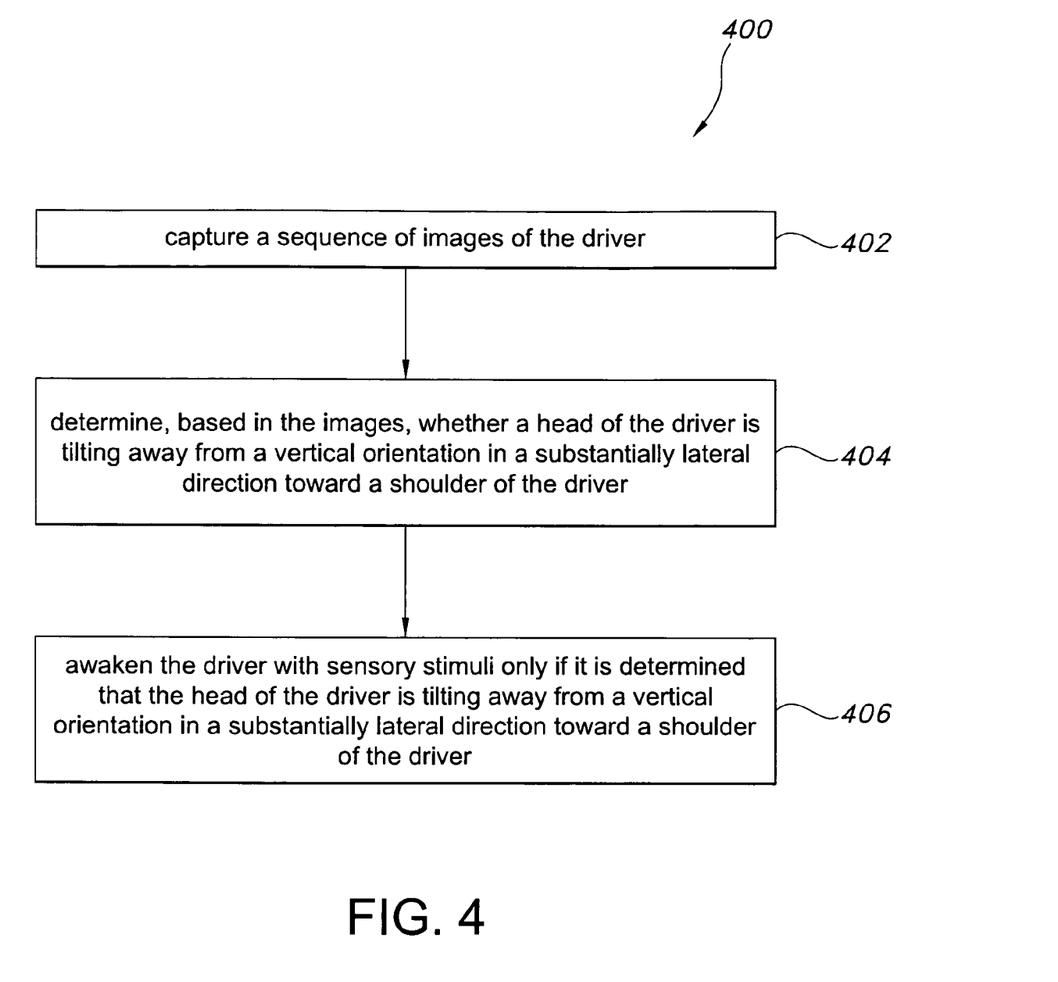
FIG. 4 is a flow chart of another embodiment of a driver drowsiness rectification method of the present invention.

Another embodiment of a method 400 of the present invention for rectifying drowsiness of a vehicle operator is illustrated in FIG. 4. In a first step 402, a sequence of images of the driver is captured. For example, CCD camera sensor 12 may capture images of the head of a driver of a vehicle. In particular embodiments, the captured images may include only the eye area of the driver's head, or an edge portion of the driver's head. The images may be captured at different points in time so as to record movement of the driver. In one embodiment, about sixteen images are captured per second.

In step 404 it is determined, based in the images, whether a head of the driver is tilting away from a vertical orientation in a substantially lateral direction toward a shoulder of the driver. That is, image processing of the captured images may determine whether the driver's head has moved from the vertical orientation indicated in solid lines in FIG. 2a to the tilted orientation indicated in dashed lines in FIG. 2a. In making this determination, image processing may measure movement of particular parts of the driver's head, such as his eyes and/or the perimeter of his head. More particularly, image processing may ascertain whether the length(s) of a certain movement or movements, such as those having reference numbers 28, 30, 32 or 34 in FIG. 2a, exceed a predetermined threshold distance.

In a final step 406, the driver is awakened with sensory stimuli only if it is determined that the head of the driver is tilting away from a vertical orientation in a substantially lateral direction toward a shoulder of the driver. In one embodiment, the driver is awakened by an audible alarm sound emitted by speaker 18. However, any other sensory stimuli effective in awakening the driver, such as automatically opening the windows of the vehicle, honking the horn, or blowing air conditioned cold air on the driver, are also within the scope of the invention.

Figure 5:
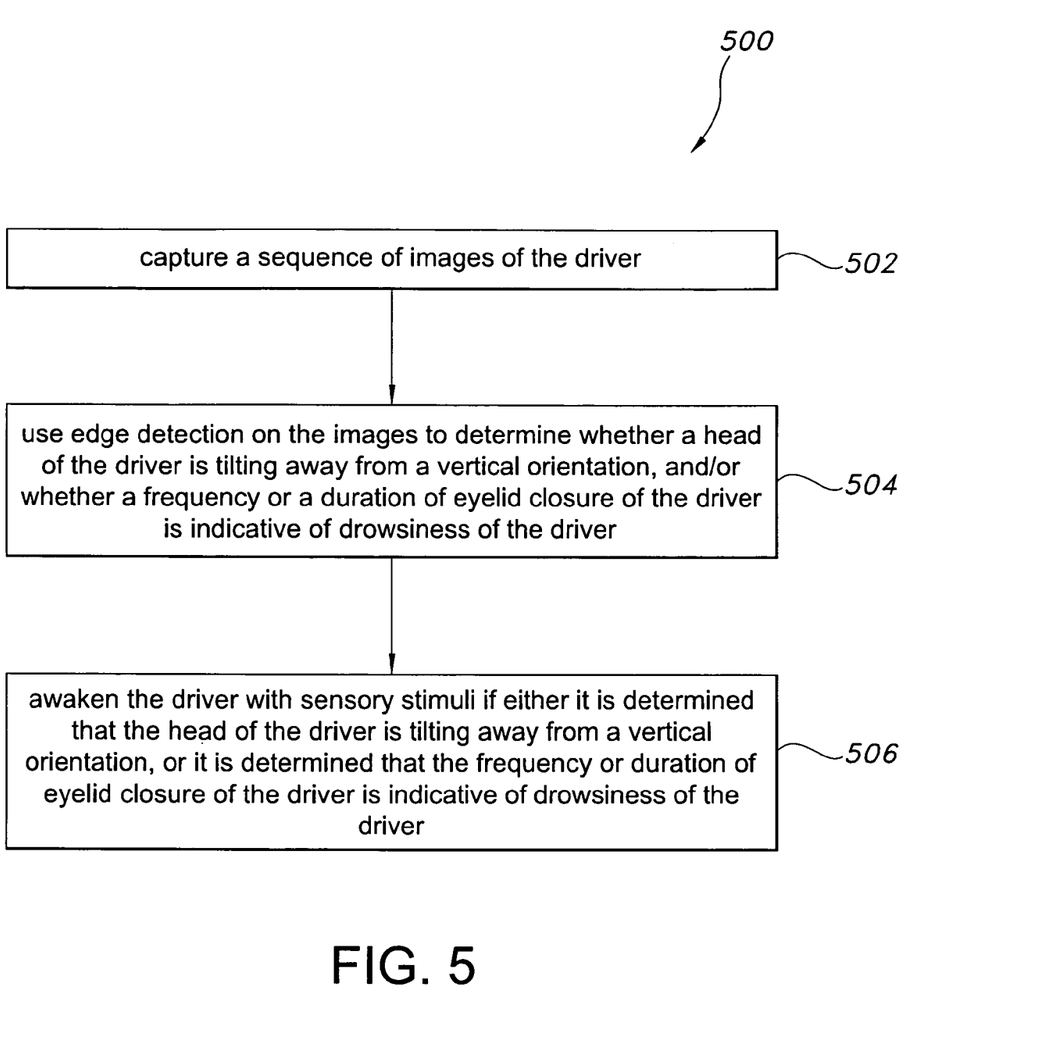
FIG. 5 is a flow chart of yet another embodiment of a driver drowsiness rectification method of the present invention.

Yet another embodiment of a method 500 of the present invention for rectifying drowsiness of a vehicle operator is illustrated in FIG. 5. In a first step 502, a sequence of images of the driver is captured. The images may be captured by a CCD camera sensor such that the images are suitable for having an edge detection algorithm performed on them.

In step 504, edge detection is used on the images to determine whether a head of the driver is tilting away from a vertical orientation, and/or whether a frequency or a duration of eyelid closure of the driver is indicative of drowsiness of the driver. In a particular embodiment, Laplacian edge detection is employed to sense movements of the driver's eye(s) or of a perimeter of his head. Edge detection as applied to the eye(s) or to the head in general may be utilized to determine tilting of the head in any direction away from the vertical, such as forward, backward, or laterally left or right as shown in FIG. 2a. It may further be determined whether a magnitude of such head tilting exceeds a threshold value. Alternatively, or in addition, Laplacian edge detection may be employed to sense the location of the driver's eye(s), and, in particular, the white portion of the eye. By monitoring the changing visibility of the whites of the eye, the frequency and/or time duration of eye blinking may be determined. It may further be determined whether the frequency and/or time duration of the eye blinking exceeds a threshold value.

In a final step 506, the driver is awakened with sensory stimuli if either it is determined that the head of the driver is tilting away from a vertical orientation; or it is determined that the frequency or duration of eyelid closure of the driver is indicative of drowsiness of the driver. The nature of the sensory stimuli may be similar to that described above with reference to step 406.

Figure 6:
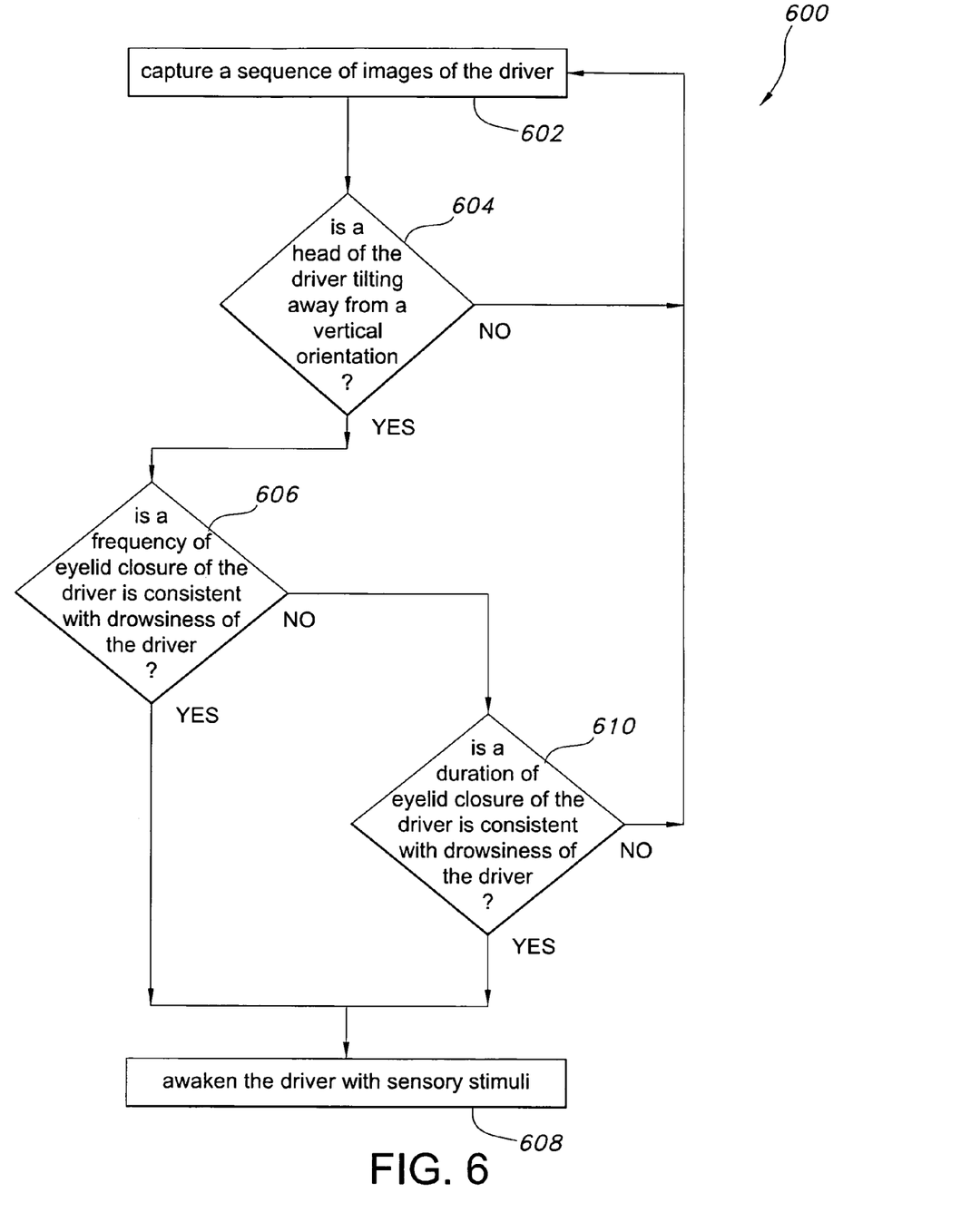
FIG. 6 is a flow chart of still another embodiment of a driver drowsiness rectification method of the present invention.

Still another embodiment of a method 600 of the present invention for rectifying drowsiness of a vehicle operator is illustrated in FIG. 6. In a first step 602, a sequence of images of the driver is captured. It is possible within the scope of the invention for the images to be captured with any type of camera or other imaging device.

In step 604 it is determined whether a head of the driver is tilting away from a vertical orientation. That is, image processing of the captured images may determine whether the driver's head has moved from the vertical orientation indicated in solid lines in FIG. 2a. The movement may be in a forward direction, backward direction, or left or right lateral direction. In making this determination, image processing may measure movement of particular parts of the driver's head, such as his eyes and/or the outer boundary of his head. More particularly, image processing may ascertain whether the length(s) of a certain movement or movements exceed a predetermined threshold distance. If it is determined in step 604 that the driver's head is tilting, then operation proceeds to step 606. Else, operation returns to step 602 where a next set of images of the driver are captured.

In step 606 it is determined whether a frequency of closure of the driver's eyelids is consistent with drowsiness of the driver. In one embodiment, after the whites of the eyes have been located, the image processing algorithm determines how often the whites of the eyes disappear and reappear, such as due to blinking. If the frequency of the whites of the eyes disappearing and reappearing exceeds a threshold frequency, as expected when the driver is drowsy, then the driver drowsiness indicated by head tilting in step 604 is found to be confirmed by a high frequency of eye blinking in step 606. Operation then proceeds to step 608, where the driver is awakened with any variety of sensory stimuli, as described above. After step 608, operation may return to step 602 where a next set of images are evaluated and a driver drowsiness determination is made based thereon. If it is determined that the driver is no longer drowsy, then the sensory stimuli may be stopped.

If it is not determined in step 606 that a frequency of the driver's eye blinking is not consistent with drowsiness, then operation proceeds to step 610, where it is determined whether a time duration of closure of the driver's eyes is consistent with drowsiness. In one embodiment, after the whites of the eyes have been located and the image processing algorithm has determined that the eyelids are closed, then the algorithm waits approximately two to three seconds and checks the immediately preceding two to three seconds of images to determine whether the eyes have remained closed. If so, then driver drowsiness as indicated by head tilting in step 604 is confirmed by eye closure in step 610 and operation proceeds to step 608, where the driver is awakened with sensory stimuli, as discussed above. If not, then operation returns to step 602 where additional captured images are evaluated for indications of driver drowsiness.

It is to be understood that it is possible for operation of either of steps 606 or 610 to proceed concurrently with that of step 604, or even to proceed before step 604. In fact, as may be readily appreciated, the time sequence of steps 604, 606 and 608 may occur in any order with the same logic and the same result occurring in step 608.

In one embodiment, a video camera with infrared capability may be interfaced to the system in order to detect eyelid closure on drivers who wear dark glasses. This allows processing of motion data in day or night conditions.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of rectifying drowsiness of a vehicle driver, comprising the steps of:
    capturing a sequence of images of the driver by use of a sensor;
    determining, based on the images, whether a head of the driver is tilting away from a vertical orientation in a substantially lateral direction toward a shoulder of the driver; and
    awakening the driver with sensory stimuli only if it is determined that the head of the driver is tilting away from a vertical orientation in a substantially lateral direction toward a shoulder of the driver.

2. The method of claim 1 wherein the determining step includes using edge detection on the images.

3. The method of claim 2 wherein the edge detection is used to ascertain a location of at least one of the driver's eyes.

4. The method of claim 3 wherein the edge detection is used to ascertain whether at least one of the driver's eyes has moved more than a threshold distance in the substantially lateral direction.

5. The method of claim 1 wherein the determining step comprises ascertaining a location of at least one of the driver's eyes.

6. The method of claim 1 comprising the further step of ascertaining that a frequency or duration of eyelid closure of the driver is consistent with drowsiness of the driver, the driver being awakened only if it is determined that the frequency or duration of eyelid closure of the driver is consistent with drowsiness of the driver.

7. The method of claim 1 wherein the determining step includes ascertaining an orientation of at least one of the driver's eyes.

8. A method of rectifying drowsiness of a vehicle driver, comprising the steps of:
    capturing a sequence of images of the driver by use of a sensor;
    using edge detection on the images to determine at least one of:
        whether a head of the driver is tilting away from a vertical orientation; and
        whether a frequency or a duration of eyelid closure of the driver is indicative of drowsiness of the driver; and
    awakening the driver with sensory stimuli if either:
        it is determined that the head of the driver is tilting away from a vertical orientation; or
        it is determined that the frequency or duration of eyelid closure of the driver is indicative of drowsiness of the driver.

9. The method of claim 8 wherein the driver is awakened only if it is determined both that the head of the driver is tilting away from a vertical orientation, and that the frequency or duration of eyelid closure of the driver is consistent with drowsiness of the driver.

10. The method of claim 8 wherein the edge detection is used to ascertain a location of at least one of the driver's eyes.

11. The method of claim 10 wherein the edge detection is used to ascertain whether at least one of the driver's eyes has moved more than a threshold distance in a substantially lateral direction.

12. The method of claim 8 wherein the using step comprises ascertaining a location of at least one of the driver's eyes.

13. The method of claim 8 wherein the edge detection is used to determine whether the driver's head is tilting in a substantially lateral direction toward a shoulder of the driver.

14. The method of claim 8 wherein the edge detection is used to determine an orientation of at least one of the driver's eyes.

15. A method of rectifying drowsiness of a vehicle driver, comprising the steps of:
    capturing a sequence of images of the driver by use of a sensor;
    determining, based in the images, whether a head of the driver is tilting away from a vertical orientation;
    ascertaining, based on the images, whether or a duration of eyelid closure of the driver is consistent with drowsiness of the driver; and
    awakening the driver with sensory stimuli only if:
        it is determined that the head of the driver is tilting away from a vertical orientation; and
        it is ascertained that the duration of eyelid closure of the driver is consistent with drowsiness of the driver.

16. The method of claim 15 wherein the determining step includes using edge detection on the images.

17. The method of claim 16 wherein the edge detection is used to ascertain whether at least one of the driver's eyes has moved more than a threshold distance in a substantially lateral direction.

18. The method of claim 16 wherein the edge detection is used to determine whether the driver's head is tilting in a substantially lateral direction toward a shoulder of the driver.

19. The method of claim 16 wherein the edge detection is used to determine an orientation of at least one of the driver's eyes.

20. The method of claim 15 wherein the determining step comprises ascertaining a location of at least one of the driver's eyes.

* * * * *

UNITED STATES PATENT AND TRADEMARK OFFICE
CERTIFICATE OF CORRECTION

PATENT NO.         : 8,063,786 B2
APPLICATION NO.    : 12/380096
DATED              : November 22, 2011
INVENTOR(S)        : Jesus Manotas, Jr.

It is certified that error appears in the above-identified patent and that said Letters Patent is hereby corrected as shown below:

IN THE CLAIMS:

Column 8, claim 15, line 59, delete "or"

Signed and Sealed this
Twenty-second Day of May, 2012

David J. Kappos
*Director of the United States Patent and Trademark Office*